(12) United States Patent
Kubo et al.

(10) Patent No.: US 10,722,682 B2
(45) Date of Patent: Jul. 28, 2020

(54) CATHETER AND BALLOON CATHETER

(71) Applicant: ASAHI INTECC CO., LTD., Seto-shi, Aichi (JP)

(72) Inventors: Yuta Kubo, Seto (JP); Moritaka Ogido, Seto (JP); Takeharu Katsurada, Nagoya (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 617 days.

(21) Appl. No.: 15/467,696

(22) Filed: Mar. 23, 2017

(65) Prior Publication Data
US 2018/0078743 A1 Mar. 22, 2018

Related U.S. Application Data

(63) Continuation of application No. PCT/JP2016/077894, filed on Sep. 21, 2016.

(51) Int. Cl.
*A61M 25/00* (2006.01)
*A61M 25/10* (2013.01)
*A61M 25/01* (2006.01)

(52) U.S. Cl.
CPC ...... *A61M 25/005* (2013.01); *A61M 25/0012* (2013.01); *A61M 25/0045* (2013.01);
(Continued)

(58) Field of Classification Search
CPC .............. A61M 25/10; A61M 25/005; A61M 25/0052; A61M 2025/1088; A61M 25/0012; A61M 25/0045–0053
See application file for complete search history.

(56) References Cited

U.S. PATENT DOCUMENTS 3,558,754 A * 1/1971 Martin ................... A41D 31/02
264/516
5,470,313 A * 11/1995 Crocker ............ A61M 25/1002
604/103.07
(Continued)

FOREIGN PATENT DOCUMENTS

EP 2767303 A1 8/2014
EP 3 025 750 A1 6/2016
(Continued)

OTHER PUBLICATIONS

Oct. 3, 2017 Notification of Reasons for Refusal issued in Japanese Patent Application No. 2016-574028.

*Primary Examiner* — Jenna Zhang
(74) *Attorney, Agent, or Firm* — Oliff PLC

(57) ABSTRACT

A catheter includes an inner layer, a reinforcement layer at least partially inside the inner layer or on an outer periphery of the inner layer, and an outer layer covering the inner layer and the reinforcement layer. The reinforcement layer has a wire wound so that a gap is present between adjacent portions of the wire. The inner layer has an uneven outer peripheral surface on which a protruded portion is formed in a location of the wire, and in which a depressed portion is formed in a location of the gap. The outer layer has a protrusion part that extends into the depressed portion of the inner layer, the protrusion part entering deeper than the reinforcement layer through the gap and extending in an axial direction of the catheter. The outer layer is not easily detached from the inner layer.

9 Claims, 13 Drawing Sheets

(52) U.S. Cl.
CPC ......... *A61M 25/10* (2013.01); *A61M 25/0052* (2013.01); *A61M 25/0108* (2013.01); *A61M 25/104* (2013.01); *A61M 2025/0183* (2013.01); *A61M 2025/1079* (2013.01); *A61M 2025/1088* (2013.01)

(56) References Cited

U.S. PATENT DOCUMENTS

| | | | |
|---|---|---|---|
| 5,647,848 A | 7/1997 | Jørgensen | |
| 5,728,063 A * | 3/1998 | Preissman | A61M 25/005 604/103.09 |
| 2009/0163833 A1 * | 6/2009 | Kinoshita | A61M 25/09 600/585 |
| 2014/0236124 A1 * | 8/2014 | Miyata | A61M 25/0045 604/527 |
| 2015/0273203 A1 | 10/2015 | Kitada et al. | |
| 2016/0136387 A1 * | 5/2016 | Otake | A61M 25/0012 604/526 |

FOREIGN PATENT DOCUMENTS

| | | |
|---|---|---|
| JP | 2008-253800 A | 10/2008 |
| JP | 2013-005823 A | 1/2013 |
| JP | 2014-155606 A | 8/2014 |
| JP | 2014-236863 A | 12/2014 |
| JP | 2015-147080 A | 8/2015 |
| JP | 2015-181886 A | 10/2015 |
| WO | 9640350 A1 | 12/1996 |
| WO | 2015/012185 A1 | 1/2015 |

* cited by examiner

CATHETER AND BALLOON CATHETER

CROSS REFERENCE TO RELATED APPLICATION

This application is a continuation of PCT/JP2016/077894 filed on Sep. 21, 2016, the contents of which are incorporated by reference herein in their entirety.

BACKGROUND

The disclosed embodiments relate to a medical device. Specifically, the disclosed embodiments relate to a catheter and balloon catheter used for diagnosing or treating a stenosis site or an obstructed segment formed inside a blood vessel or digestive organ.

A stenosis site or an obstructed segment formed in a blood vessel, bile duct, pancreatic duct, or the like may restrict the flow of blood, bile (gall), pancreatic fluid or the like, respectively. Catheters are widely used for diagnosing or treating such a stenosis site or an obstructed segment.

In general, a catheter includes a tubular inner layer, an outer layer covering the outer periphery of the inner layer, and a reinforcement layer arranged between the inner layer and the outer layer. In such a catheter where the inner layer is joined with the outer layer through the reinforcement layer, it is difficult to improve the joining strength between the inner layer and the outer layer.

As one known way of improving the joining strength between the inner layer and the outer layer, a protruding portion may be provided in the inner layer, the protruding portion protruding to the outer layer side through a gap in the reinforcement layer and extending in the axial direction so as to enter into the outer layer (see WO 2015/012185).

However, in the catheter described in WO 2015/012185, the protruding portion of the inner layer only extends in one direction from the proximal end to the distal end. Therefore, disadvantageously, the outer layer may be susceptible to detaching from the inner layer when the outer layer is dragged in the distal direction by a stenosis site or an obstructed segment. Further, the protruding portion of the inner layer is only provided on the outside of the reinforcement layer. Stress may therefore be concentrated at the joining region between the protruding portion of the inner layer and the outer layer due to bending of the catheter when the catheter is inserted through a curved blood vessel, bile duct, pancreatic duct, or the like. Therefore, the problem remains that the outer layer may be susceptible to detaching from the inner layer.

SUMMARY

The disclosed embodiments have been derived in view of these circumstances. An object of the disclosed embodiments is to provide a catheter and balloon catheter in which an outer layer is not easily detached from an inner layer even when the outer layer is pulled in the axial direction (either of the distal and proximal directions).

The above object can be achieved by virtue of the following structures.

A catheter of the disclosed embodiments includes a tubular inner layer; a reinforcement layer provided inside the inner layer or on an outer periphery of the inner layer; and an outer layer covering the reinforcement layer and inner layer. The reinforcement layer has a wire wound so that a gap is present between adjacent portions of the wire. The inner layer has an uneven outer peripheral surface on which a protruded portion is formed in a location of the wire, and in which a depressed portion is formed in a location of the gap. The outer layer has a protrusion part that extends into the depressed portion of the inner layer, the protrusion part entering deeper than the reinforcement layer through the gap and extending in an axial direction of the catheter. The joining strength between the inner layer and the outer layer of the catheter is improved, and the risk that the outer layer will detach from the inner layer is reduced due to the anchoring effect of the protrusion part of the outer layer caught in the reinforcement layer even when the outer layer is dragged in the axial direction (either of the distal or proximal directions) by a stenosis site or an obstructed segment.

The length of the protrusion part of the outer layer in the axial direction of the catheter may be longer than the length of the gap of the reinforcement layer in the axial direction of the catheter. In this case, the anchoring effect between the protrusion part of the outer layer and the reinforcement layer can be enhanced not only in the axial direction but also in the radial direction, which in turn can further reduce the risk that the outer layer will detach from the inner layer.

The catheter may be a balloon catheter in which a balloon is joined to the outer layer. In this case, the outer layer has an uneven outer peripheral surface on which a protruded portion is formed in a location of the wire, and a depressed portion is formed in a location of the gap, so that the uneven outer peripheral surface of the outer layer corresponds to (mates with) the uneven outer peripheral surface of the inner layer. The balloon enters into the depressed portion of the outer layer. This configuration can enhance the joining strength between the balloon and the outer layer. Therefore, the risk that the balloon will detach from outer layer can be reduced even when the balloon is inflated in the radial direction. Moreover, the configuration in which the balloon enters into the depressed portion of the outer layer can allow the thickness of the balloon to be thinner while maintaining the joining strength between the balloon and the outer layer, resulting in improved insertability of the balloon catheter into a blood vessel, bile duct, pancreatic duct, or the like.

DETAILED DESCRIPTION OF EMBODIMENTS

Figure 1:
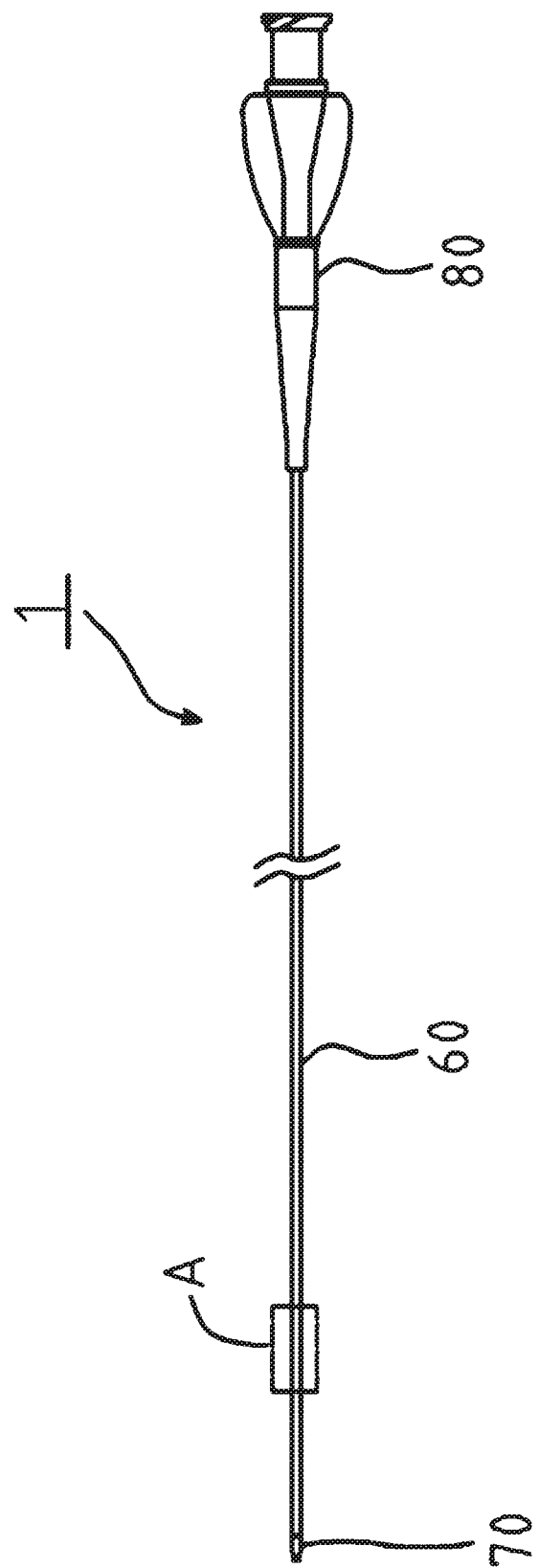
FIG. 1 shows an overall view of an entire catheter according to the disclosed embodiments.
Figure 2:
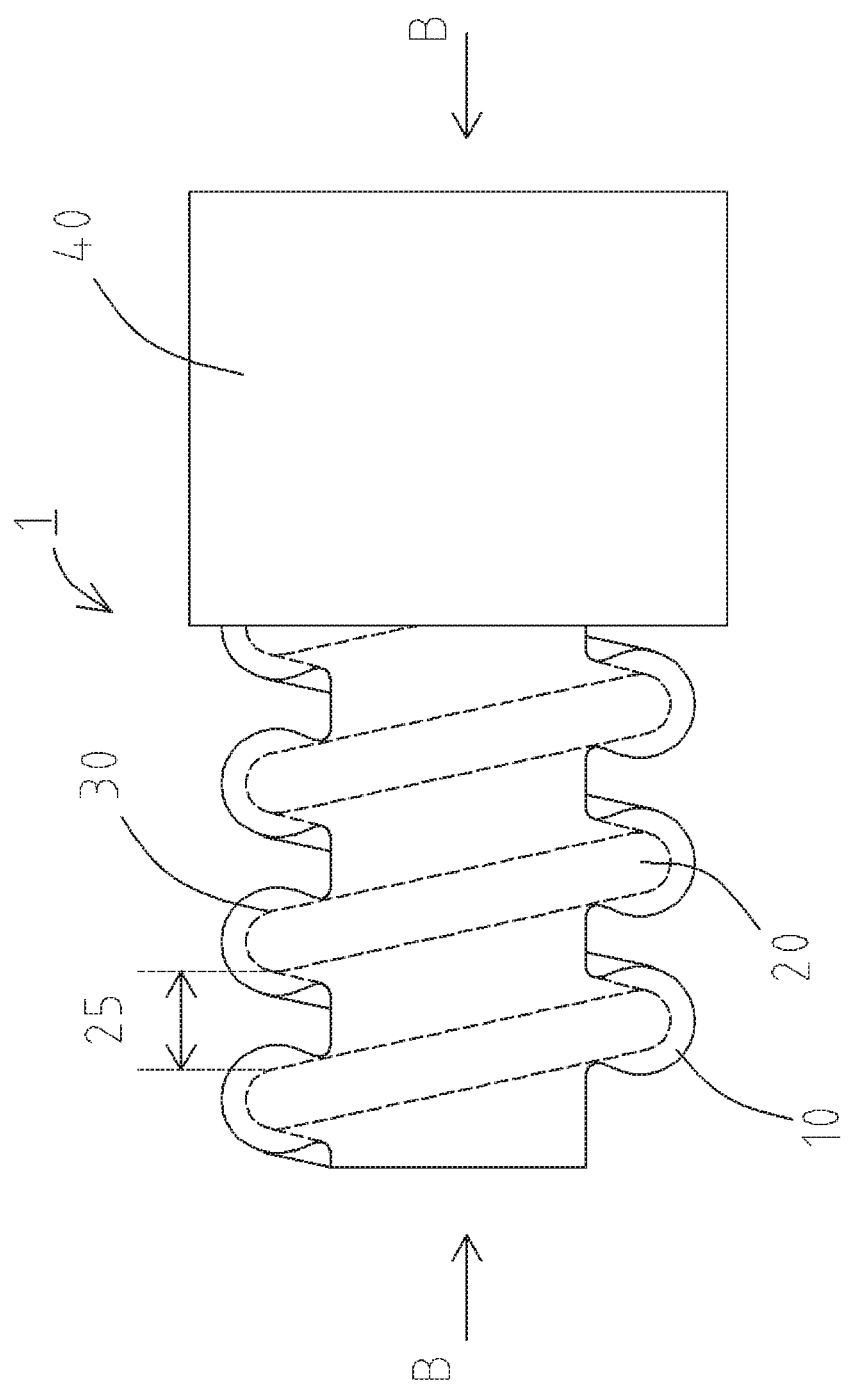
FIG. 2 shows an enlarged view of section A in FIG. 1.
Figure 3:
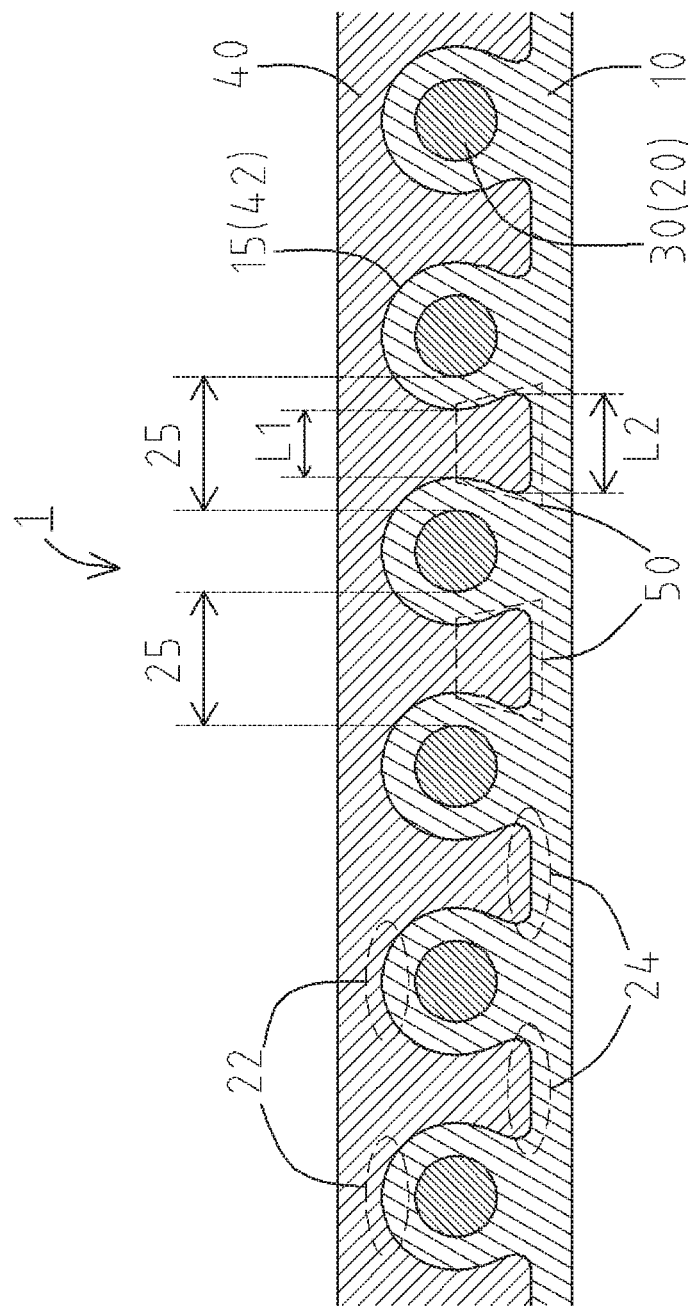
FIG. 3 shows a cross-sectional view along the line B-B in FIG. 2.

A catheter 1 according to the disclosed embodiments will be described with reference to FIGS. 1 to 3. Throughout the figures, the left side corresponds to the distal end (the front end), which is to be inserted into the body, and the right side corresponds to the proximal end (the base end), which is to be operated by an operator such as a physician. FIG. 2 shows an enlarged view of section A in FIG. 1, and FIG. 3 shows a cross-sectional view along the line B-B in FIG. 2.

The catheter 1 may be used, for example, to diagnose or treat a stenosis site or an obstructed segment. As shown in FIG. 1, the catheter 1 includes a catheter shaft 60, a tip 70 joined to a distal end of the catheter shaft 60, and a connector 80 joined to a proximal end of the catheter shaft 60.

As shown in FIG. 2, the catheter shaft 60 includes an inner layer 10; a reinforcement layer (coil body) 30 present inside the inner layer 10; and an outer layer 40 covering the reinforcement layer 30. In other words, the reinforcement layer 30 is present entirely within the inner layer 10 near an outer peripheral surface of the inner layer 10, and is surrounded by the inner layer 10. The reinforcement layer 30 has a wire 20 wound so that a gap 25 is present between adjacent portions (windings) of the wire 20. Note that a part of the outer layer 40 is not shown in FIG. 2 for better understanding.

The inner layer 10 is formed of a resin, through which a guide wire or another catheter can be inserted. There is no particular limitation on the resin material used for forming the inner layer 10, but polytetrafluoroethylene (PTFE) is used for purposes of this discussion.

The coil body as the reinforcement layer 30 is formed inside the inner layer 10. The coil body is formed by winding the wire 20 in the clockwise direction toward a distal end of the catheter 1. Stainless steel (SUS304) is used as a material for the wire 20 of the coil body for purposes of this discussion, but the material is not limited to this. For example, metal materials such as tungsten and Ni—Ti alloys as well as resin materials such as reinforced plastics (polyether ether ketone, PEEK) may be used. Note that the wire 20 of the coil body may be wound in the counterclockwise direction toward the distal end of the catheter 1.

The outer layer 40 is made of a resin and covers the inner layer 10 and the reinforcement layer 30. There is no particular limitation on the resin material for forming the outer layer 40, and polyamide, polyamide elastomer, polyester, polyurethane, and the like may be used.

The tip 70 is made of a resin and is joined to the distal end of the catheter shaft 60 as described above (see FIG. 1). There is no particular limitation on the resin for forming the tip 70, and example resins include polyurethane, polyurethane elastomer, and the like. Further, the tip 70 may contain a radiopaque powder. As an example, when the tip 70 contains a radiopaque powder (for example, tungsten powder) in the range of between about 65 w % and about 90 w %, an operator such as a medical doctor can accurately detect the position of the catheter 1 under coronary angiography.

As shown in FIG. 3, the inner layer 10 has an uneven outer peripheral surface 15 on which a protruded portion 22 is formed in a location of the wire 20, and in which a depressed portion 24 is formed in a location of the gap 25. Further, the outer layer 40 has a protrusion part 50 that extends into the depressed portion 24 of the inner layer 10, the protrusion part 50 entering deeper than the reinforcement layer 30 through the gap 25 and extending in an axial direction of the catheter 1.

The protrusion part 50 of the outer layer 40 has an approximately trapezoidal cross-sectional shape. An axial length L2 of a lower base of the protrusion part 50 near the depressed portion 24 of the inner layer 10 is longer than an axial length L1 of an upper base of the protrusion part 50 near the center of the wire 20 (in other words, at a location where the distance between the adjacent protruded portions 22 is the smallest) (L2>L1). Further, the outer layer 40 has an uneven inner peripheral surface 42 that corresponds to and mates with the uneven outer peripheral surface 15 of the inner layer 10.

According to the catheter 1, the outer layer 40 has the protrusion part 50 in a location of the depressed portion 24 of the inner layer 10, the protrusion part 50 entering deeper than the reinforcement layer 30 through the gap 25 and extending in the axial direction of the catheter 1. This can improve the joining strength between the inner layer 10 and the outer layer 40. Further, the risk that the outer layer 40 will detach from the inner layer 10 can be reduced by virtue of the anchoring effect in which the protrusion part 50 of the outer layer 40 is caught in the reinforcement layer 30 even when the outer layer 40 is dragged in the axial direction (either of the distal and proximal directions) at a stenosis site or an obstructed segment upon insertion of the catheter 1 into a blood vessel, bile duct, pancreatic duct, or the like.

Figure 4:
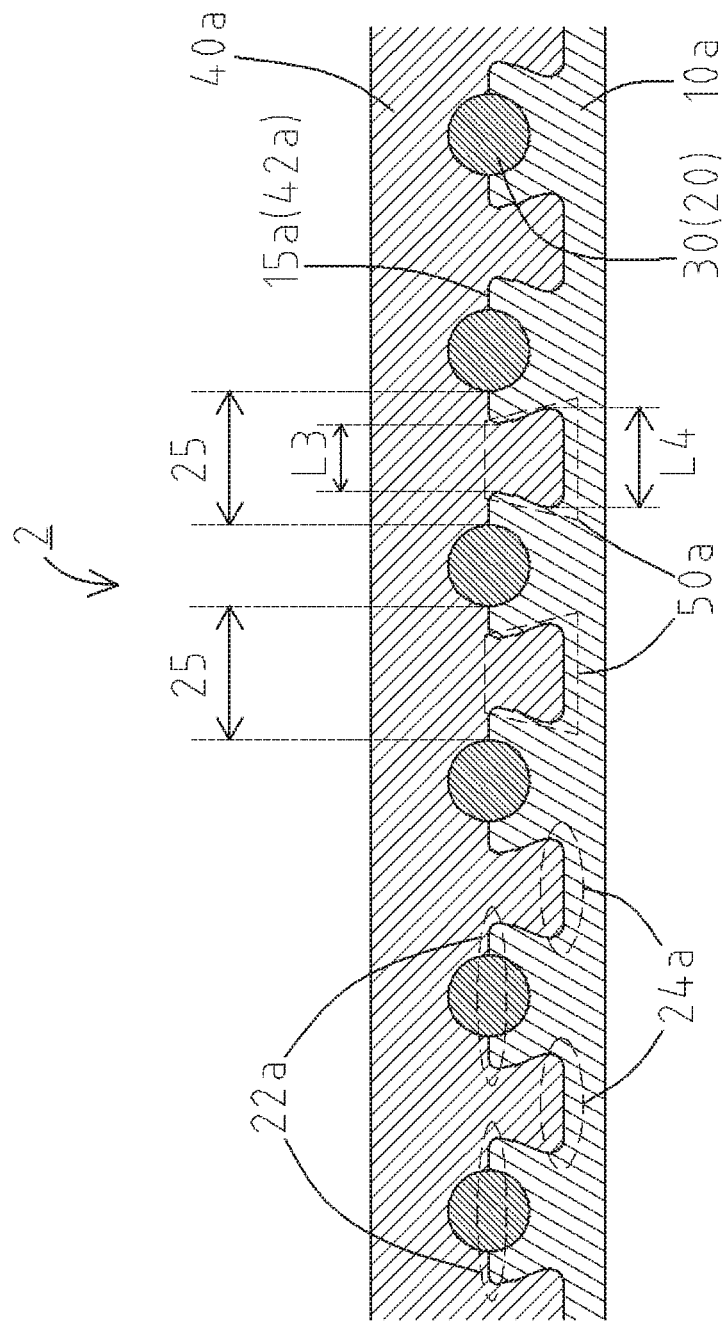
FIG. 4 shows a cross-sectional view of a catheter according to the disclosed embodiments.

Next, a catheter 2 according to the disclosed embodiments will be described with reference to FIG. 4. Only differences from the catheter 1 shown in FIG. 3 will be described. In the catheter 2, an inner peripheral surface of the coil body as the reinforcement layer 30 is buried inside an inner layer 10a while the outer peripheral surface of the coil body is buried inside an outer layer 40a. The inner layer 10a has an uneven outer peripheral surface 15a on which a protruded portion 22a is formed in a location of the wire 20, and in which a depressed portion 24a is formed in a location of the gap 25. Further, the outer layer 40a has a protrusion part 50a that extends into the depressed portion 24a of the inner layer 10a, the protrusion part 50a entering deeper than the reinforcement layer 30 through the gap 25 and extending in an axial direction of the catheter 2.

The protrusion part 50a of the outer layer 40a has an approximately trapezoidal cross-sectional shape as in the protrusion part 50 of the catheter 1. An axial length L4 of a lower base of the protrusion part 50a near the depressed portion 24a of the inner layer 10a is longer than an axial length L3 of an upper base of the protrusion part 50a near the center of the wire 20 (in other words, at a location where the distance between the adjacent protruded portions 22a is the smallest) (L4>L3). Further, the outer layer 40a has an uneven inner peripheral surface 42a that corresponds to the uneven outer peripheral surface 15a of the inner layer 10a.

According to the catheter 2, the outer layer 40a has the protrusion part 50a in a location of the depressed portion 24a of the inner layer 10a, the protrusion part 50a entering deeper than the reinforcement layer 30 through the gap 25 and extending in the axial direction as in the catheter 1. This can improve the joining strength between the inner layer 10a and the outer layer 40a. Further, the risk that the outer layer 40a will detach from the inner layer 10a can be reduced by virtue of the anchoring effect in which the protrusion part 50a of the outer layer 40a is caught in the reinforcement layer 30 even when the outer layer 40a is dragged in the axial direction (either of the distal and proximal directions)

at a stenosis site or an obstructed segment upon insertion of the catheter 2 into a blood vessel, bile duct, pancreatic duct, or the like.

Figure 5:
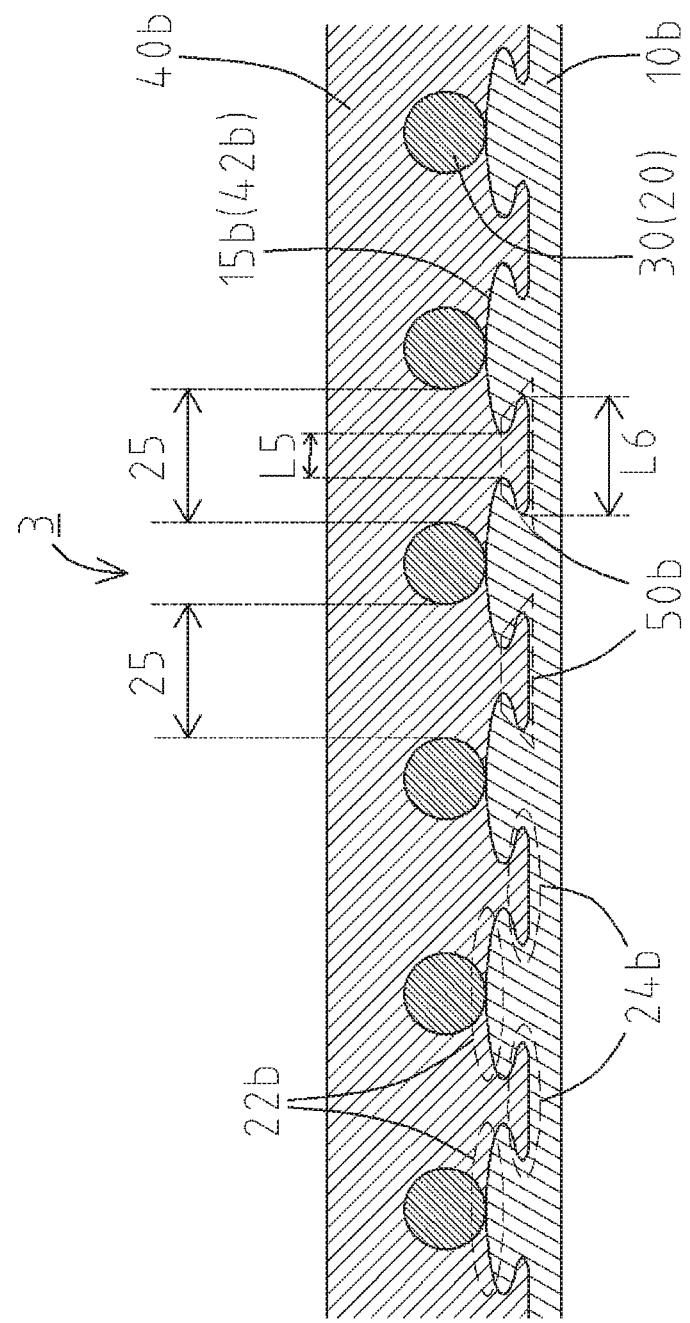
FIG. 5 shows a cross-sectional view of a catheter according to the disclosed embodiments.

Next, a catheter 3 according to the disclosed embodiments will be described with reference to FIG. 5. Only differences from the catheter 1 shown in FIG. 3 will be described. In the catheter 3, the coil body as the reinforcement layer 30 is formed on an outer periphery of an inner layer 10*b*. The inner layer 10*b* has an uneven outer peripheral surface 15*b* on which a protruded portion 22*b* is formed in a location of the wire 20, and in which a depressed portion 24*b* is formed in a location of the gap 25. Further, an outer layer 40*b* has a protrusion part 50*b* that extends into the depressed portion 24*b* of the inner layer 10*b*, the protrusion part 50*b* entering deeper than the reinforcement layer 30 through the gap 25 and extending in an axial direction of the catheter 3.

The protrusion part 50*b* of the outer layer 40*b* has an approximately trapezoidal cross-sectional shape as in the protrusion part 50 of the catheter 1. An axial length L6 of a lower base of the protrusion part 50*b* near the depressed portion 24*b* of the inner layer 10*b* is longer than an axial length L5 of an upper base of the protrusion part 50*b* at a location where the distance between the adjacent protruded portions 22*b* is the smallest (L6>L5). Further, the outer layer 40*b* has an uneven inner peripheral surface 42*b* that corresponds to the uneven outer peripheral surface 15*b* of the inner layer 10*b*.

According to the catheter 3, the outer layer 40*b* has the protrusion part 50*b* in a location of the depressed portion 24*b* of the inner layer 10*b*, the protrusion part 50*b* entering deeper than the reinforcement layer 30 through the gap 25 and extending in the axial direction of the catheter 3. This can improve the joining strength between the inner layer 10*b* and the outer layer 40*b*. Further, the risk that the outer layer 40*b* will detach from the inner layer 10*b* can be reduced by virtue of the anchoring effect in which the protrusion part 50*b* of the outer layer 40*b* is caught in the reinforcement layer 30 even when the outer layer 40*b* is dragged in the axial direction (either of the distal and proximal directions) at a stenosis site or an obstructed segment upon insertion of the catheter 3 into a blood vessel, bile duct, pancreatic duct, or the like.

Figure 6:
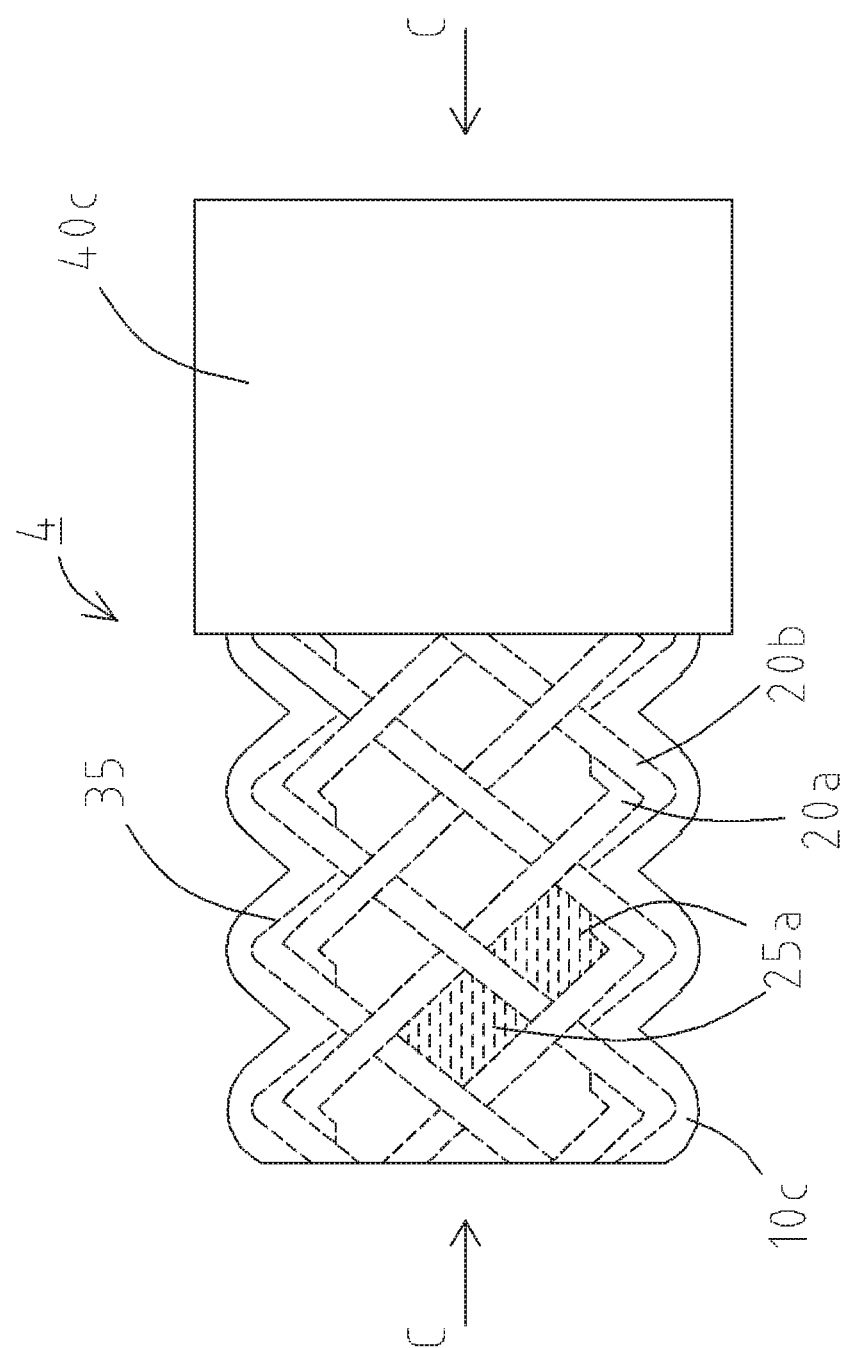
FIG. 6 shows an enlarged view of a catheter according to the disclosed embodiments.

Next, a catheter 4 according to the disclosed embodiments will be described with reference to FIGS. 6 and 7. Only differences from the catheter 1 shown in FIGS. 2 and 3 will be described. The catheter 4 includes an inner layer 10*c*; a reinforcement layer (braid) 35 present inside the inner layer 10; and an outer layer 40*c* covering the reinforcement layer 35 (see FIG. 6). The reinforcement layer 35 has multiple wires 20*a*, 20*b* interwoven with each other so that a gap 25*a* is present between adjacent portions of the wires 20*a*, 20*b*. Note that a part of the outer layer 40*c* is not shown in FIG. 6 for better understanding.

The reinforcement layer 35 includes a first wire 20*a* and a second wire 20*b* interwoven with each other in a web-like (mesh-like) fashion, in which the first wire 20*a* is wound in the clockwise direction toward a distal end of the catheter 4, and the second wire 20*b* is wound in the counterclockwise direction toward the distal end. In the catheter 4, a total of 16 wires of 8 first wires 20*a* and 8 second wires 20*b* (8×8) are interwoven with each other to form the reinforcement layer (braid) 35.

The first wires 20*a* and the second wires 20*b* of the reinforcement layer 35 may be made of the same material, or may be made of different materials. For purposes of this discussion, first wires 20*a* made of tungsten and second wires 20*b* made of stainless steel (SUS 304) are used, but the materials are not particularly limited to these, and non-metal resin materials (for example, reinforced plastics) may be used.

Figure 7:
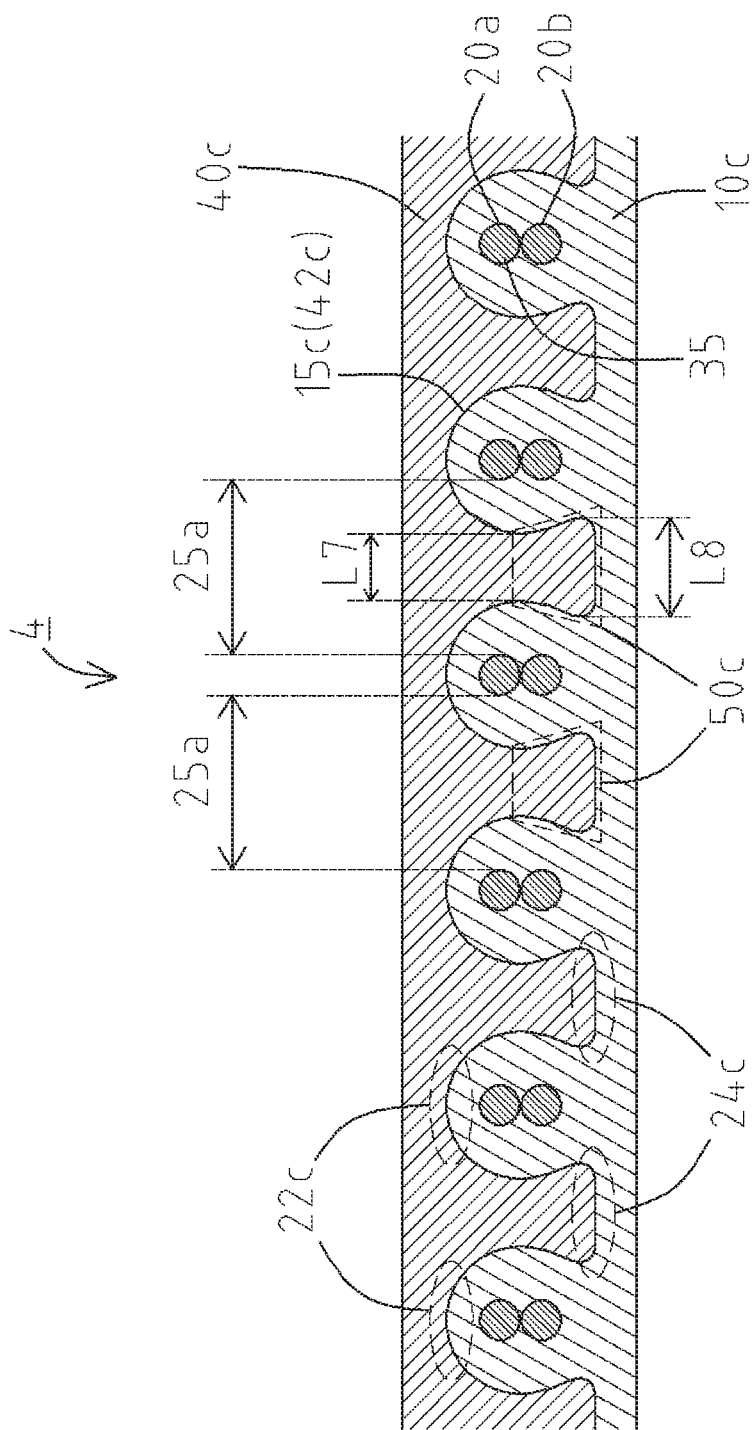
FIG. 7 shows a cross-sectional view along the line C-C in FIG. 6.

As shown in FIG. 7, the inner layer 10*c* has an uneven outer peripheral surface 15*c* on which a protruded portion 22*c* is formed in a location of the first wire 20*a* and the second wire 20*b*, and a depressed portion 24*c* is formed in a location of the gap 25*a*. Further, the outer layer 40*c* has a protrusion part 50*c* that extends into the depressed portion 24*c* of the inner layer 10*c*, the protrusion part 50*c* entering deeper than the reinforcement layer 35 through the gap 25*a* and extending in an axial direction of the catheter 4.

The protrusion part 50*c* of the outer layer 40*c* has an approximately cross-sectional trapezoidal shape. An axial length L8 of a lower base of the protrusion part 50*c* near the depressed portion 24*c* of the inner layer 10*c* is longer than an axial length L7 of an upper base of the protrusion part 50*c* near the centers of the wire 20*a* and the wire 20*b* of the reinforcement layer 35 (in other words, at a location where the distance between the adjacent protruded portions 22*c* is the smallest) (L8>L7). Further, the outer layer 40*c* has an uneven inner peripheral surface 42*c* that corresponds to the uneven outer peripheral surface 15*c* of the inner layer 10*c*.

According to the catheter 4, the outer layer 40*c* has the protrusion part 50*c* in a location of the depressed portion 24*c* of the inner layer 10*c*, the protrusion part 50*c* entering deeper than the reinforcement layer 35 through the gap 25 and extending in the axial direction of the catheter 4. This can improve the joining strength between the inner layer 10*c* and the outer layer 40*c*. Further, the risk that the outer layer 40*c* will detach from the inner layer 10*c* can be reduced by virtue of the anchoring effect in which the protrusion part 50*c* of the outer layer 40*c* is caught in the reinforcement layer 35 even when the outer layer 40*c* is dragged in the axial direction (either of the distal and proximal directions) at a stenosis site or an obstructed segment upon insertion of the catheter 4 into a blood vessel, bile duct, pancreatic duct, or the like.

Figure 8:
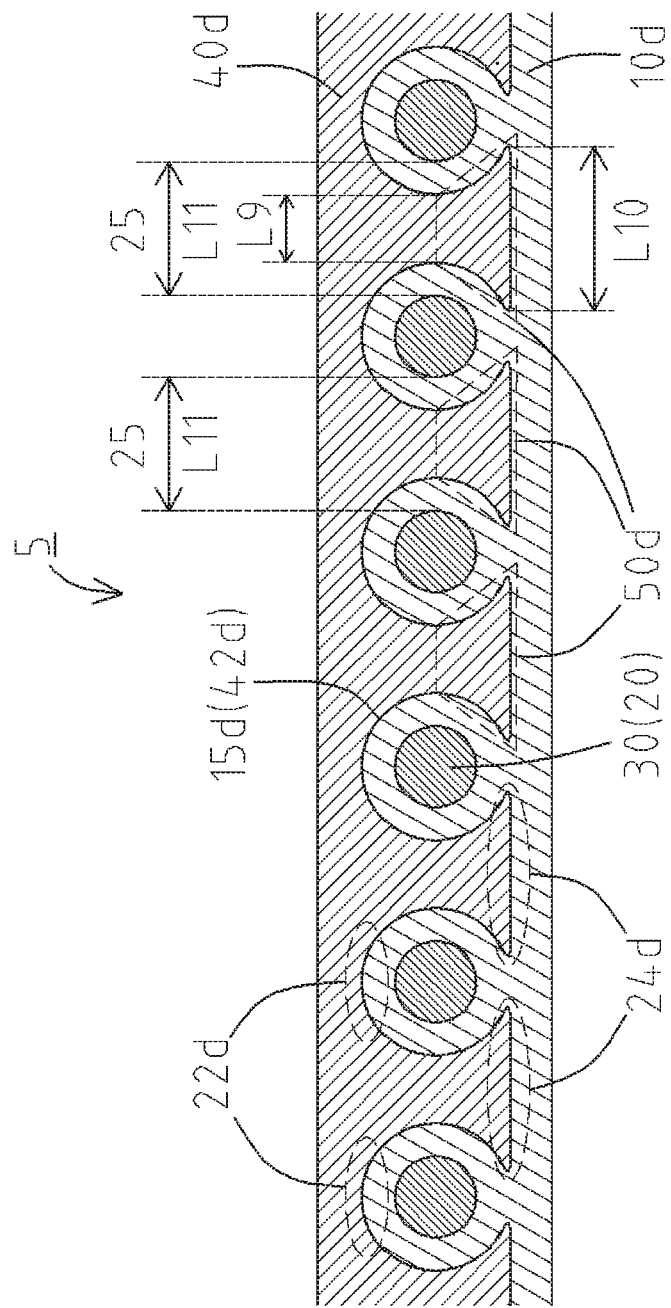
FIG. 8 shows a cross-sectional view of a catheter according to the disclosed embodiments.

Next, a catheter 5 according to the disclosed embodiments will be described with reference to FIG. 8. Only differences from the catheter 1 shown in FIG. 3 will be described. In the catheter 5, an inner layer 10*d* has an uneven outer peripheral surface 15*d* on which a protruded portion 22*d* is formed in a location of the wire 20, and in which a depressed portion 24*d* is formed in a location of the gap 25. Further, the outer layer 40*d* has a protrusion part 50*d* that extends into the depressed portion 24*d* of the inner layer 10*d*, the protrusion part 50*d* entering deeper than the reinforcement layer 30 through the gap 25 and extending in the axial direction of the catheter 5.

The protrusion part 50*d* of the outer layer 40*d* has an approximately trapezoidal cross-sectional shape as in the protrusion part 50 of the catheter 1. An axial length L10 of a lower base of the protrusion part 50*d* near the depressed portion 24*d* of the inner layer 10*d* (in other words, the largest length of the protrusion part 50*d* of the outer layer 40*d* in the axial direction) is longer than an axial length L9 of an upper base of the protrusion part 50*d* near the center of the wire 20 (in other words, at a location where the distance between the adjacent protruded portions 22*d* is the smallest) (L10>L9). Further, the axial length L10 of the lower base of the protrusion part 50*d* is longer than an axial length L11 of the gap 25 of the reinforcement layer 30 in the axial direction of the catheter 5 (L10>L11) (see FIG. 8). Further, the outer layer 40*d* has an uneven inner peripheral surface 42*d* that corresponds to the uneven outer peripheral surface 15*d* of the inner layer 10*d*.

As described above, according to the catheter 5, the length L10 of the lower base of the protrusion part 50*d* of the outer layer 40*d* is longer than the length L11 of the gap 25 of the reinforcement layer 30 in the axial direction of the catheter 5. This can reduce the risk that the outer layer 40*d* will detach from the inner layer 10*d* in the radial direction because the protrusion part 50*d* of the outer layer 40*d* is caught in the reinforcement layer 30 even when the outer layer 40*d* is dragged outward in the radial direction. Thereby, the anchoring effect between the protrusion part 50*d* of the outer layer 40*d* and the reinforcement layer 30 can be enhanced not only in the axial direction but also in the radial direction.

Next, a balloon catheter 6 according to the disclosed embodiments will be described with reference to FIGS. 9 and 10. FIG. 10 shows an enlarged view of section D in FIG. 9. The balloon catheter 6 is used for expanding and treating, for example, a stenosis site or an obstructed segment.

Figure 9:
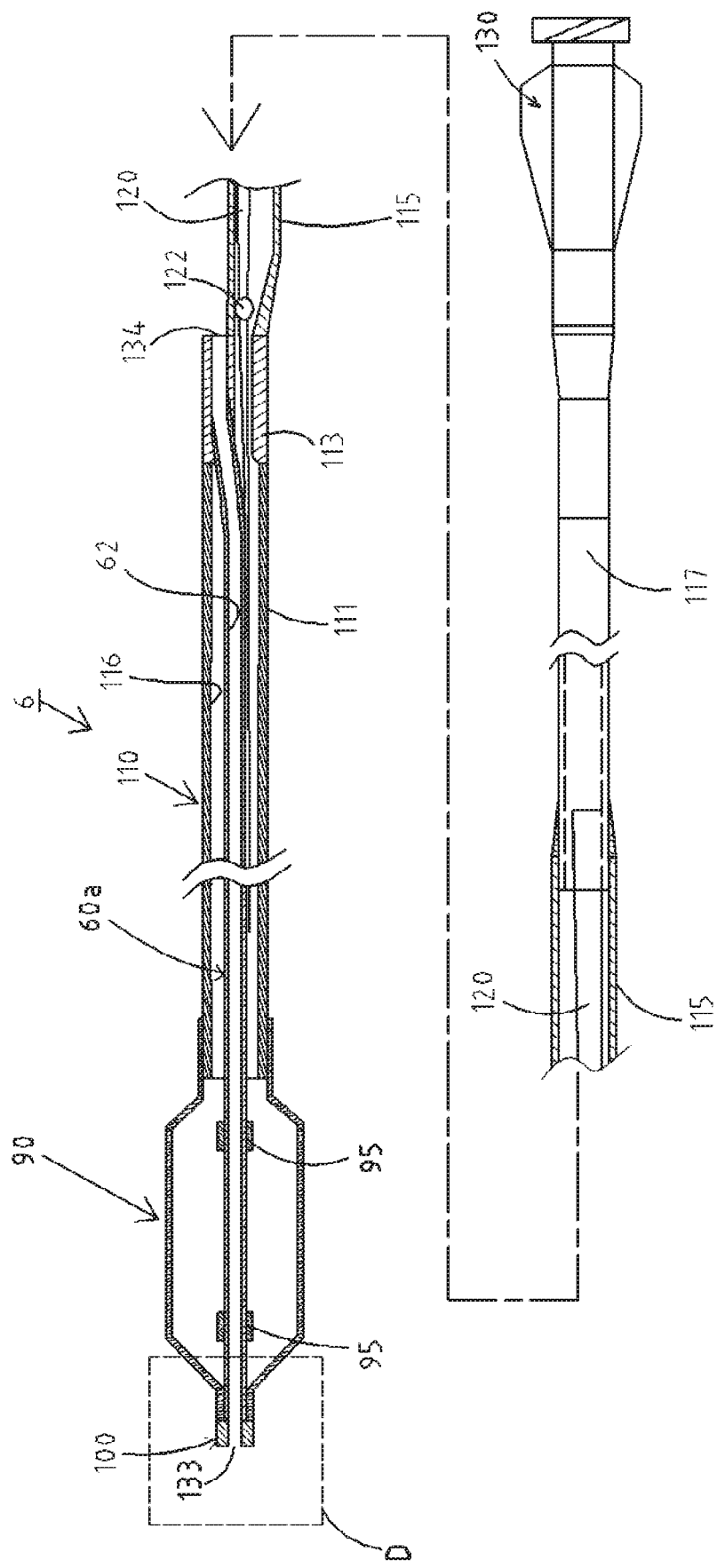
FIG. 9 shows an overall view of an entire catheter according to the disclosed embodiments.
Figure 10:
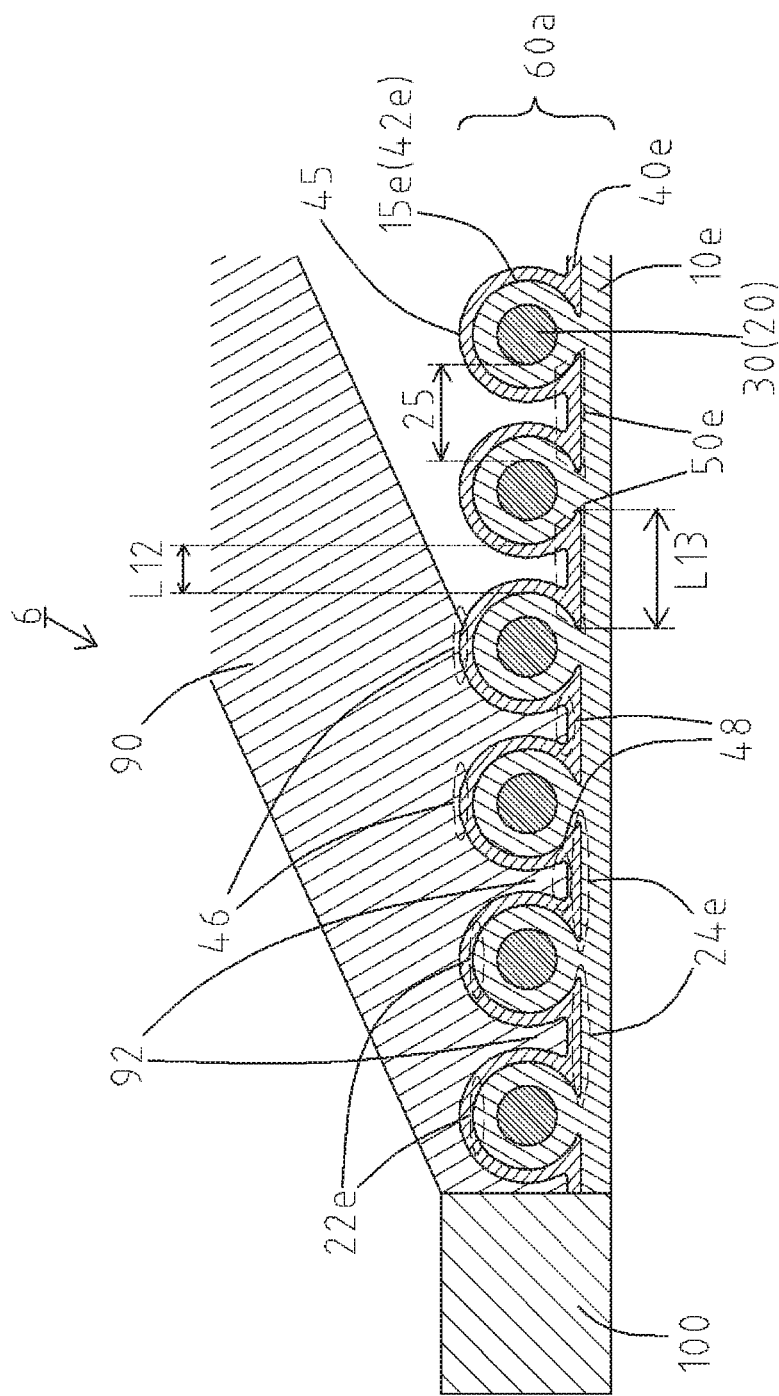
FIG. 10 shows an enlarged view of section D in FIG. 9.

As shown in FIG. 9, the balloon catheter 6 includes a balloon 90, a tip 100, an outer shaft 110, an inner shaft 60*a*, a reinforcement body 120, and a connector 130.

The balloon 90 for expanding a stenosis site or obstructed segment includes a member made of a resin. A distal end of the balloon 90 is joined to a distal end of the inner shaft 60*a* and the tip 100, and a proximal end of the balloon 90 is joined to a distal end of the outer shaft 110.

The outer shaft 110 is a tubular member which constitutes an inflation lumen 116 for supplying a liquid such as contrast medium and physiological saline in order to inflate the balloon 90. The outer shaft 110 includes, in order from the distal end, a distal end outer shaft portion 111, a guide wire port portion 113, a middle outer shaft portion 115, and a proximal end outer shaft portion 117. The distal end outer shaft portion 111 and the middle outer shaft portion 115 are tubes made of a resin such as polyamide, polyamide elastomer, polyolefin, polyester, and polyester elastomer. The distal end outer shaft portion 111, the middle outer shaft portion 115, and the inner shaft 60*a* are joined to each other at the guide wire port portion 113.

The inner shaft 60*a* is inserted in the distal end outer shaft portion 111, and the inflation lumen 116 described above is formed between the distal end outer shaft portion 11*l* and the inner shaft 60*a*.

The proximal end outer shaft portion 117 is a metal tubular member which is referred to as a so-called hypotube. A distal end of the proximal end outer shaft portion 117 is inserted into and joined to a proximal end of the middle outer shaft portion 115. The connector 130 is attached to a proximal end of the proximal end outer shaft portion 117. When a liquid such as contrast medium and physiological saline for inflating the balloon 90 is supplied from an indeflator (not shown) which can be attached to the connector 130, the liquid is allowed to pass through the inflation lumen 116 to inflate the balloon 90. Note that there is no particular limitation on the material of the proximal end outer shaft portion 117, but stainless steel (SUS 302, SUS 304) and superelastic alloys such as Ni—Ti alloys may be used.

The inner shaft 60*a* forms a guide wire lumen 62 for inserting a guide wire therein. Further, a proximal end of the inner shaft 60*a* is joined to the guide wire port portion 113 of the outer shaft 110 to form a proximal end side guide wire port 134. Guide wires can be exchanged by an operator through the above proximal end side guide wire port 134.

The tip 100 is joined to the distal end of the inner shaft 60*a* and the distal end of the balloon 90. The tip 100 is made of a resin with plasticity. There is no particular limitation on the material, but polyurethane, polyurethane elastomer, and the like may be used. Further, the distal end tip 100 has a distal end side guide wire port 133 at its distal end.

The reinforcement body 120 is attached to an inner periphery of the distal end of the proximal end outer shaft portion 17. The reinforcement body 120 has a circular cross-section, and is a tapered metal wire member having a diameter decreasing toward the distal end. There is no particular limitation on the material of the reinforcement body 120, but stainless steel (SUS 304) and superelastic alloys such as Ni—Ti alloys may be used. The above reinforcement body 120 extends to the distal end outer shaft portion 111 through the middle outer shaft portion 115 and the guide wire port portion 113. Further, the reinforcement body 120 includes a pusher part 122 capable of abutting (pushing on) the guide wire port portion 113.

Two markers 95 are attached to an outer periphery of the inner shaft 60*a* in the inside of the balloon 90. Thereby, an operator such as a physician can accurately detect the position of the balloon 90 under coronary angiography, facilitating reliable expansion of a stenosis site or obstructed segment.

As shown in FIG. 10, the above inner shaft 60*a* includes an inner layer 10*e*; the reinforcement layer 30 present inside the inner layer 10*e*; and an outer layer 40*e* covering the inner layer 10*e* and the reinforcement layer 30.

The inner layer 10*e* has an uneven outer peripheral surface 15*e* on which a protruded portion 22*e* is formed in a location of the wire 20, and in which a depressed portion 24*e* is formed in a location of the gap 25. Further, the outer layer 40*e* has a protrusion part 50*e* that extends into the depressed portion 24*e* of the inner layer 10*e*, the protrusion part 50*e* entering deeper than the reinforcement layer 30 through the gap 25 and extending in an axial direction of the balloon catheter 6.

The protrusion part 50*e* of the outer layer 40*e* has an approximately trapezoidal cross-sectional shape as in the protrusion part 50 of the catheter 1. An axial length L13 of a lower base of the protrusion part 50*e* near the depressed portion 24*e* of the inner layer 10*e* (in other words, the largest length of the protrusion part 50*e* of the outer layer 40*e* in the axial direction) is longer than an axial length L12 of an upper base of the protrusion part 50*e* near the center of the wire 20 (in other words, at a location where the distance between the adjacent protruded portions 22*e* is the smallest) (L13>L12). Further, the outer layer 40*e* has an uneven inner peripheral surface 42*e* that corresponds to the uneven outer peripheral surface 15*e* of the inner layer 10*e*.

In the inner shaft 60*a*, the outer layer 40*e* has the protrusion part 50*e* in the depressed portion 24*e* of the inner layer 10*e*, the protrusion part 50*e* entering deeper than the reinforcement layer 30 through the gap 25 and extending in the axial direction of the balloon catheter 6. This can improve the joining strength between the inner layer 10*e* and the outer layer 40*e*. Further, the risk that the outer layer 40*e* will detach from the inner layer 10*e* can be reduced by virtue of the anchoring effect in which the protrusion part 50*e* of the outer layer 40*e* is caught in the reinforcement layer 30 even when the outer layer 40*e* is dragged in the axial direction (either of the distal and proximal directions) upon insertion of the balloon catheter 6 into a blood vessel, bile duct, pancreatic duct, or the like.

Further, the outer layer 40*e* has an uneven outer peripheral surface 45 on which the protruded portion 46 is formed in a location of the wire 20, and the depressed portion 48 is formed in a location of the gap 25, the uneven outer peripheral surface 45 being arranged along the outer peripheral surface 15e of the inner layer 10e.

The balloon 90 enters into the depressed portion 48 of the outer layer 40e, and is joined to the outer peripheral surface 45 of the outer layer 40e. In other words, a protruding portion 92 is provided at the distal end of a balloon 90 so that the protruding portion 92 enters into the depressed portion 48 of the outer layer 40e.

The protruding portion 92 of the balloon 90 is joined to the depressed portion 48 of the outer layer 40e as described above. This configuration can enhance the joining strength between the balloon 90 and the outer layer 40e. Therefore, the risk that the balloon 90 will detach from the outer layer 40e can be reduced even when the balloon 90 is inflated in the radial direction. Further, the balloon 90 enters into the depressed portion 48 of the outer layer 40e. This configuration can allow the thickness of the balloon 90 to be thinner while maintaining the joining strength between the balloon 90 and the outer layer 40e, resulting in improved insertability of the balloon catheter 6 into a blood vessel, bile duct, pancreatic duct, or the like.

Note that any of the catheters 1 to 5 may be used as the inner shaft 60a of the balloon catheter 6 as shown in FIGS. 9 and 10.

Figure 11:
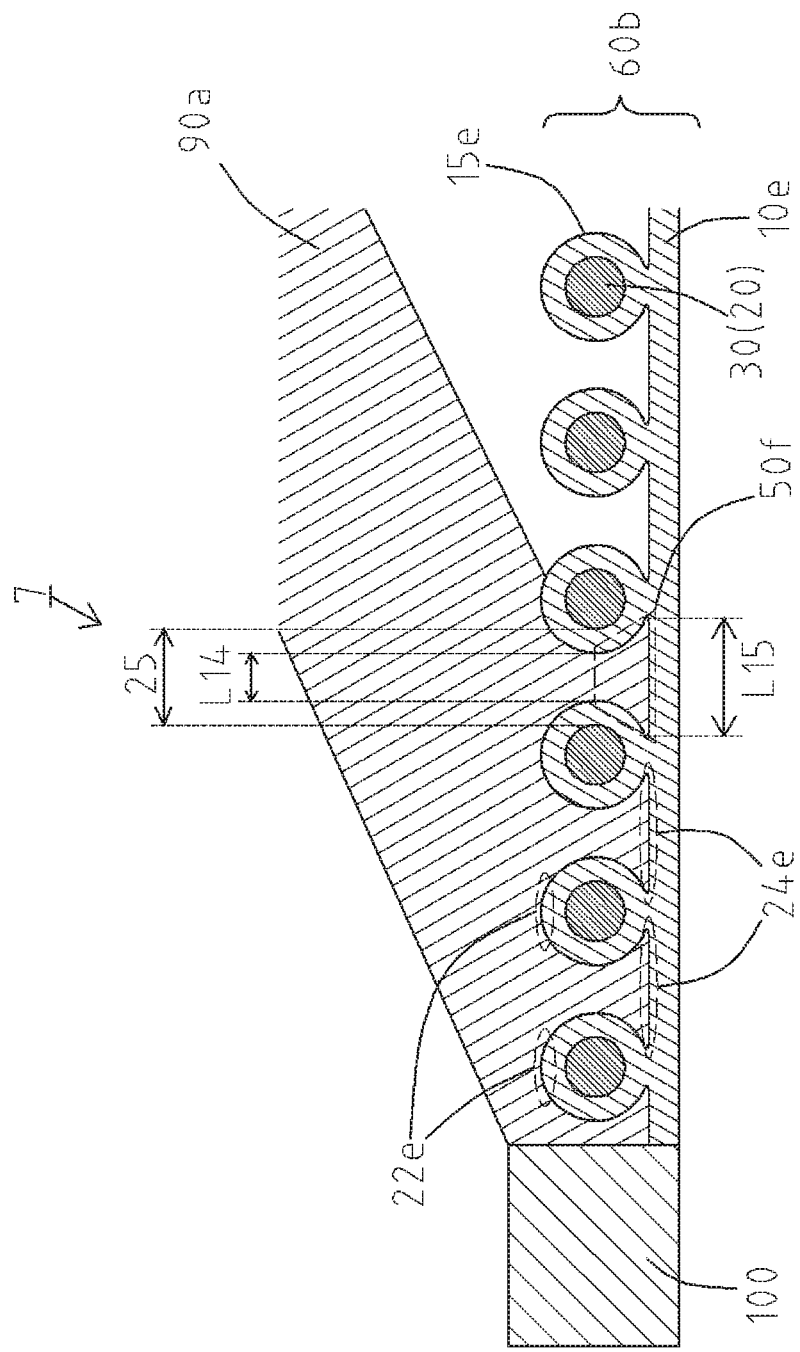
FIG. 11 shows a cross-sectional view of a balloon catheter according to the disclosed embodiments.

Further, the inner shaft 60a of the balloon catheter 6 includes the inner layer 10e, the reinforcement layer 30, and the outer layer 40e as a cover. However, the configuration is not limited to this. For example, as shown in FIG. 11, in a balloon catheter 7 according to the disclosed embodiments, an inner shaft 60b includes only the inner layer 10e and the reinforcement layer (coil body) 30 present inside the inner layer 10e. In other words, unlike the balloon catheter 6, the inner shaft 60b does not have the outer layer 40e.

Only differences from the balloon catheter 6 shown in FIG. 10 will be described. In the balloon catheter 7, a balloon 90a enters into the depressed portion 24e of the inner layer 10e, and is joined to the outer peripheral surface 15e of the inner layer 10e. Specifically, the balloon 90a has a protrusion part 50f that extends into the depressed portion 24e of the inner layer 10e, the protrusion part 50f entering deeper than the reinforcement layer 30 through the gap 25 and extending in an axial direction of the balloon catheter 7.

The protrusion part 50f of the balloon 90a has an approximately trapezoidal cross-sectional shape. An axial length L15 of a lower base of the protrusion part 50f near the depressed portion 24e of the inner layer 10e is longer than an axial length L14 of an upper base of the protrusion part 50f near the center of the wire 20 (in other words, at a location where the distance between the adjacent protruded portions 22 is the smallest) (L15>L14).

In the balloon catheter 7, the balloon 90a has the protrusion part 50f in the depressed portion 24e of the inner layer 10e, the protrusion part 50f entering deeper than the reinforcement layer 30 through the gap 25 and extending in the axial direction of the balloon catheter 7. This can improve the joining strength between the inner layer 10e and the balloon 90a. Further, the risk that the balloon 90a will detach from the inner layer 10e can be reduced by virtue of the anchoring effect in which the protrusion part 50f of the balloon 90a is caught in the reinforcement layer 30 even when the balloon 90a is dragged in the axial direction (either of the distal and proximal directions) at a stenosis site or an obstructed segment upon insertion of the balloon catheter 7 into a blood vessel, bile duct, pancreatic duct, or the like.

Further, the balloon 90a enters into the depressed portion 24e of the inner layer 10e. This configuration can allow the thickness of the balloon 90a to be thinner while maintaining the joining strength between the balloon 90a and the inner layer 10e, resulting in improved insertability of the balloon catheter 7 into a blood vessel, bile duct, pancreatic duct or the like.

Further, the protrusion parts 50, 50a, 50b, 50c, 50d, and 50e of the outer layers 40, 40a, 40b, 40c, 40d, and 40e; and the protrusion part 50f of the balloon 90a in the catheters 1 to 5 and the balloon catheters 6 and 7 as described above are shown to have approximately trapezoidal cross-sectional shapes. However, they may have any cross-sectional shape.

Figure 12:
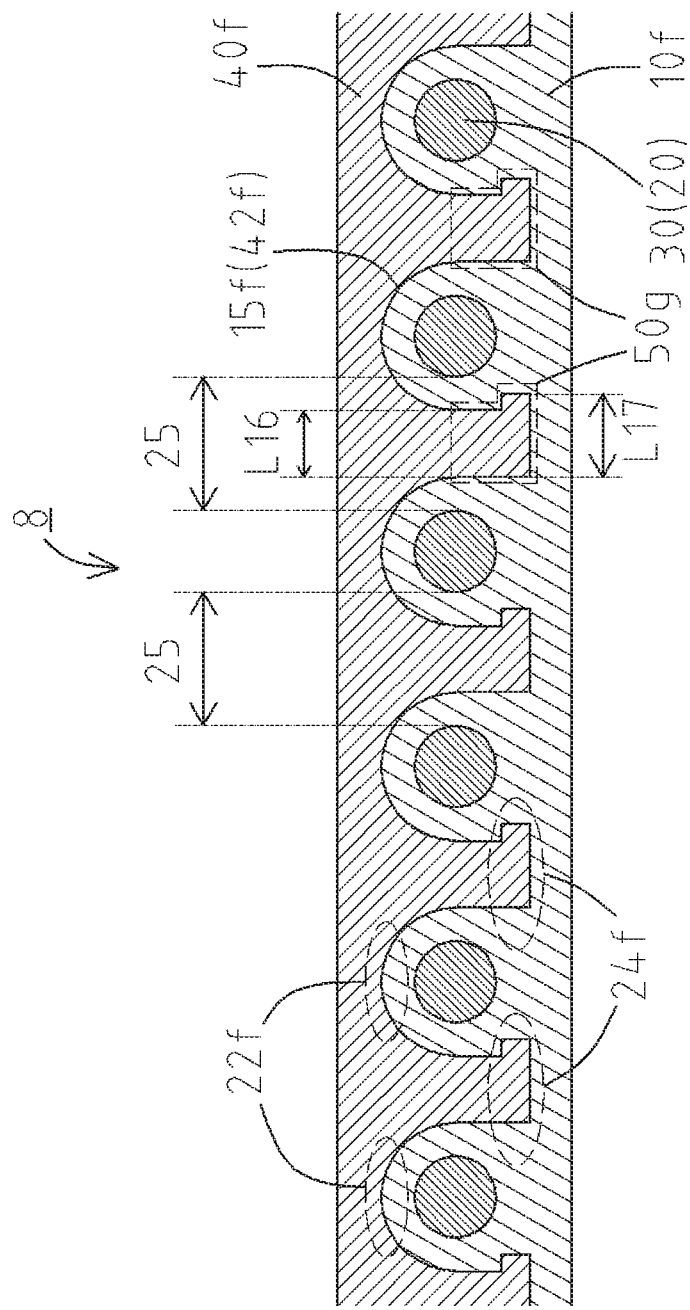
FIG. 12 shows a cross-sectional view of a catheter according to the disclosed embodiments.

For example, in a catheter 8 according to the disclosed embodiments as shown in FIG. 12, an inner layer 10f has an uneven outer peripheral surface 15f on which a protruded portion 22f is formed in a location of the wire 20, and a depressed portion 24f is formed in a location of the gap 25. Further, the outer layer 40f has a protrusion part 50g that extends into the depressed portion 24f of the inner layer 10f, the protrusion part 50g entering deeper than the reinforcement layer 30 through the gap 25 and extending in the axial direction.

The protrusion part 50g of the outer layer 40f has an L-like cross-sectional shape. An axial length L17 of a lower base of the protrusion part 50g near the depressed portion 24f of the inner layer 10f is longer than an axial length L16 of an upper base of the protrusion part 50g near the center of the wire 20 (in other words, at a location where the distance between the adjacent protruded portions 22f is the smallest) (L17>L16). Further, the outer layer 40f has an uneven inner peripheral surface 42f that corresponds to the uneven outer peripheral surface 15f of the inner layer 10f.

Note that in the catheter 8, the protrusion part 50g of the outer layer 40f extends only in the proximal direction, but the configuration is not limited to this. It may be configured to extend only in the distal direction of the catheter 8.

Figure 13:
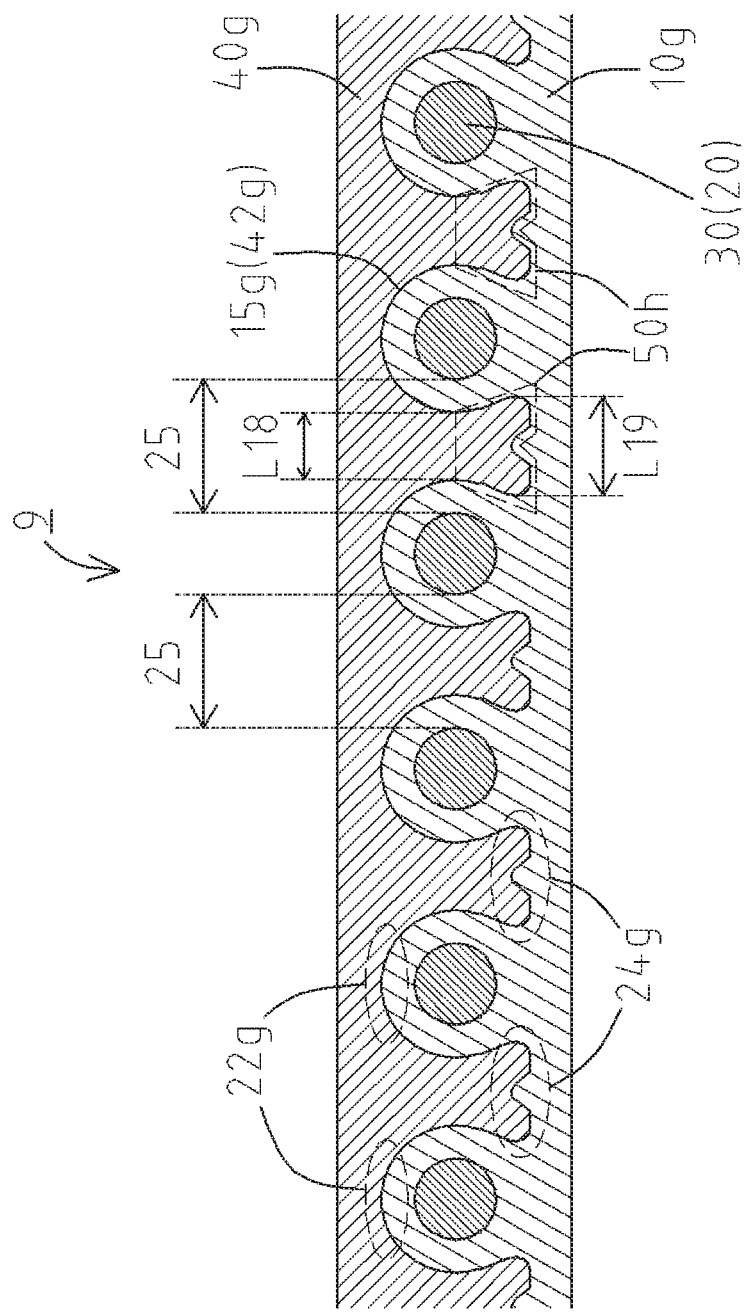
FIG. 13 shows a cross-sectional view of a catheter according to the disclosed embodiments.

Further, in a catheter 9 according to the disclosed embodiments as shown in FIG. 13, an inner layer 10g has an uneven outer peripheral surface 15g on which a protruded portion 22g is formed in a location of the wire 20, and in which a depressed portion 24g is formed in a location of the gap 25. Further, an outer layer 40g has a protrusion part 50h that extends into the depressed portion 24g of the inner layer 10g, the protrusion part 50h entering deeper than the reinforcement layer 30 through the gap 25 and extending in the axial direction of the catheter 9.

The protrusion part 50h of the outer layer 40g bifurcates near the depressed portion 24g of the inner layer 10g. An axial length L19 of a lower base of the protrusion part 50h near the depressed portion 24g of the inner layer 10g is longer than an axial length L18 of an upper base of the protrusion part 50h near the center of the wire 20 (in other words, at a location where the distance between the adjacent protruded portions 22g is the smallest) (L19>L18). Further, the outer layer 40g has an uneven inner peripheral surface 42g that corresponds to the uneven outer peripheral surface 15g of the inner layer 10g.

Further, the coil body 30 and the braid 35 are shown as examples of the reinforcement layer in the above descriptions, but the configuration is not limited to this. For example, a reinforcement layer in which a gap is included as a spiral slit provided in a hypotube (a metal tube) may be used in the catheters 1 to 5, 8, and 9 and the balloon catheters 6 and 7.

What is claimed is:
1. A catheter comprising:
   a tubular inner layer;
   a reinforcement layer present at least partially inside the inner layer or on an outer periphery of the inner layer, the reinforcement layer having a wire wound so that a gap is present between adjacent portions of the wire; and an outer layer covering the inner layer and the reinforcement layer, wherein:

the inner layer has an uneven outer peripheral surface on which a protruded portion is formed in a location of the wire, and in which a depressed portion is formed in a location of the gap, the outer layer has a protrusion part that extends into the depressed portion of the inner layer, the protrusion part extending beyond the reinforcement layer through the gap in a radial direction of the catheter and having a lower base that extends in an axial direction of the catheter, and an axial length L2 of the lower base of the protrusion part near the depressed portion of the inner layer is longer than an axial length L1 of an upper base of the protrusion part near the center of the wire.

2. The catheter according to claim 1, wherein the axial length L2 is longer than a length of the gap of the reinforcement layer in the axial direction of the catheter.

3. A balloon catheter comprising:
the catheter according to claim 1; and
a balloon joined to the outer layer,
wherein:
the outer layer has an uneven outer peripheral surface on which a protruded portion is formed in the location of the wire, and in which a depressed portion is formed in the location of the gap, the uneven outer peripheral surface of the outer layer being arranged along the outer peripheral surface of the inner layer, and
the balloon enters into the depressed portion of the outer layer.

4. A balloon catheter comprising:
the catheter according to claim 2; and
a balloon joined to the outer layer,
wherein:
the outer layer has an uneven outer peripheral surface on which a protruded portion is formed in the location of the wire, and in which a depressed portion is formed in the location of the gap, the uneven outer peripheral surface of the outer layer being arranged along the outer peripheral surface of the inner layer, and
the balloon enters into the depressed portion of the outer layer.

5. The catheter according to claim 1, wherein the reinforcement layer is present entirely inside the inner layer.

6. The catheter according to claim 1, wherein an inner peripheral surface of the reinforcement layer is present inside the inner layer, and an outer peripheral surface of the reinforcement layer is exposed to the outer layer.

7. The catheter according to claim 1, wherein the reinforcement layer is present on the outer periphery of the inner layer.

8. The catheter according to claim 1, wherein the reinforcement layer is a coil body.

9. The catheter according to claim 1, wherein the reinforcement layer is a braid having first wires wound in a first direction and second wires wound in a second direction, the first wires and the second wires being wound so that the gap is present between adjacent portions of the first wires and the second wires.

* * * * *